(12) United States Patent
Swords

(10) Patent No.: US 7,066,962 B2
(45) Date of Patent: Jun. 27, 2006

(54) COMPOSITE SURGICAL IMPLANT MADE FROM MACROPOROUS SYNTHETIC RESIN AND BIOGLASS PARTICLES

(75) Inventor: Greg Swords, Atlanta, GA (US)

(73) Assignee: Porex Surgical, Inc., Newnan, GA (US)

( * ) Notice: Subject to any disclaimer, the term of this patent is extended or adjusted under 35 U.S.C. 154(b) by 0 days.

(21) Appl. No.: 10/334,151

(22) Filed: Dec. 31, 2002

(65) Prior Publication Data

US 2004/0019389 A1    Jan. 29, 2004

Related U.S. Application Data

(60) Provisional application No. 60/397,609, filed on Jul. 23, 2002.

(51) Int. Cl.
*A61F 2/02* (2006.01)
(52) U.S. Cl. .................................................. 623/17.18
(58) Field of Classification Search ............. 623/17.18, 623/23.72, 23.61, 23.74, 23.76; 428/314.2
See application file for complete search history.

(56) References Cited

U.S. PATENT DOCUMENTS

| | | | |
|---|---|---|---|
| 4,676,796 A | 6/1987 | Merwin et al. | |
| 4,775,646 A | 10/1988 | Hench et al. | |
| 4,839,215 A | 6/1989 | Starling et al. | |
| 5,211,664 A | 5/1993 | Tepic et al. | |
| 5,501,706 A | 3/1996 | Arenberg | |
| 5,645,934 A | 7/1997 | Marcolongo et al. | |
| 5,648,301 A | 7/1997 | Ducheyne | |
| 5,681,872 A | 10/1997 | Erbe | |
| 5,728,753 A | 3/1998 | Bonfield et al. | |
| 5,899,939 A | 5/1999 | Boyce et al. | |
| 5,977,204 A | 11/1999 | Boyan et al. | |
| 6,027,742 A | 2/2000 | Lee | |
| 6,121,172 A | 9/2000 | Marcolongo et al. | |
| 6,200,347 B1 | 3/2001 | Anderson et al. | |
| 6,214,049 B1 | 4/2001 | Gayer et al. | |
| 6,240,926 B1 * | 6/2001 | Chin Gan et al. | 128/898 |
| 6,294,041 B1 | 9/2001 | Boyce et al. | |
| 6,299,930 B1 | 10/2001 | Marotta et al. | |
| 6,328,990 B1 | 12/2001 | Ducheyne et al. | |
| 6,350,284 B1 | 2/2002 | Tormala et al. | |
| 6,599,516 B1 * | 7/2003 | Knaack | 424/423 |
| 6,756,060 B1 * | 6/2004 | Greenspan et al. | 424/489 |
| 6,767,550 B1 * | 7/2004 | Genin et al. | 424/426 |
| 6,808,585 B1 * | 10/2004 | Boyce et al. | 156/244.11 |
| 6,852,330 B1 * | 2/2005 | Bowman et al. | 424/426 |
| 2003/0065400 A1 * | 4/2003 | Beam et al. | 623/23.51 |
| 2004/0006153 A1 * | 1/2004 | Seppala et al. | 523/113 |

FOREIGN PATENT DOCUMENTS

| | | |
|---|---|---|
| JP | 2353968 | 3/2001 |
| WO | WO 88/03417 | 5/1988 |

(Continued)

*Primary Examiner*—Corrine McDermott
*Assistant Examiner*—Thomas J Sweet
(74) *Attorney, Agent, or Firm*—Venable LLP; Andrew C. Aitken

(57) ABSTRACT

A cranio-maxillofacial implant material that is made of a macroporous (greater than 100 microns in diameter) interconnecting porous polyethylene structure with bioactive glass particles dispersed throughout the porous polyethylene structure, is disclosed. The Implant provides augmentation or replacement of cranio-maxillofacial tissues when implanted subperiosteally or within cranio-maxillofacial soft tissue. The addition of the bioactive glass particles to the porous polyethylene implant structure provides for faster fibrovascular ingrowth into the implant material.

19 Claims, 2 Drawing Sheets

FOREIGN PATENT DOCUMENTS

| WO | WO 00/71083 | 11/2000 |
| WO | WO 01/12106 | 2/2001 |

* cited by examiner

COMPOSITE SURGICAL IMPLANT MADE FROM MACROPOROUS SYNTHETIC RESIN AND BIOGLASS PARTICLES

This invention is directed to an improved surgical implant matrix for filling the space of large cavities in the body. The applicant claims the benefit of the U.S. Provisional Applicant No. 60/397,609 filed on Jul. 23, 2002.

BACKGROUND OF THE INVENTION

This invention relates surgical implants and more particularly to cranio-maxillofacial reconstruction and augmentation. The invention is directed to an improved implant material that is particularly suited for reconstruction and augmentation of cranio-maxillofacial structures and tissues.

A surgeon is sometimes presented circumstances where portions of an patient's face or other areas of the head have been damaged, lost or are missing due to trauma, surgical removal of cancerous or otherwise diseased tissue, or congenital defects. In these instances it is useful to implant a material completely within the body to replace or augment the damaged or lost tissue. In other instances, it is desirable to implant a material to enhance facial features for cosmetic reasons.

A commonly used material for replacement or augmentation of facial and head tissues is a graft taken from other parts of the patient's head, face or body. When the graft is from the patent's own body it is referred to as an autograft. An alternative to autografts are allografts which describe materials harvested from human donor tissue that typically have been processed to minimize infection or triggering an auto-immune response. Another alternative is the use of xenografts which describes implants that originate from animal tissue. Yet a further surgical implant material are referred to as alloplasts which describe implants made from synthetic materials.

Autografts require the material be surgically harvested from another part of the patient's body, and are accordingly subject to the problems of lack of availability and donor site morbidity associated with a second or multiple surgical sites required to harvest the material. Further, in many situations, autografts are subject to shrinkage, resorption or changes in shape that may compromise the desired reconstructive or aesthetic result.

Allografts and xenografts carry the possibility of viral infection transmission or prion transmission, limited availability, and they are also subject to shrinkage, resorption or changes in shape that may compromise the desired reconstructive or aesthetic result.

Synthetic implant materials do not have the problems described above that are associated with allografts and xenografts but have other difficulties. The most common synthetic alloplastic materials are titanium, solid silicone, polymethylmethacrylate (PMMA) otherwise known as acrylic, expanded polytetrafluoroethylene ("ePTFE"), porous polyethylene ("pPE"), and bioactive glass.

Bioactive glass or bioglass is supplied as granules, typically with a particle size range of 90 to 900 microns. Bioactive glass particles have been used as a bone replacement materials and studies have demonstrated that the glasses will aid osteogenisis in a physiologic system. Further, the bonds between the bone and glass, as described in U.S. Pat. No. 4,851,046 has been found to be strong, stable and without toxic effects. The particles may be mixed with saline or body fluids to form a somewhat cohesive granular mixture that can be placed into tissue defect sites. The spaces between the granules allows for fibrovascular ingrowth. In view of the nature of the matrix, bioactive glass does not have the structural integrity of the other alloplasts described here.

Bioglass is commercially available from U.S. Biomaterials of Alachua, Fla. which sells the material having a composition of approximately 45% silicon dioxide, 45% sodium oxide, and the remaining 10% calcium and phosphorus oxide. Bioglass is sold in granular form under the trademark NOVABONE. An exemplary composition and application of bioglass is disclosed in U.S. Pat. No. 6,338,751 to Litkowski et al.

Bioglass has properties that appear to accelerate the rate of fibrovascular ingrowth or bone ingrowth into its macroporous structure. When bioglass is wet with saline or body fluids and placed within the body, it releases by dissolution silicon, sodium, calcium and phosphorous ions into the surrounding area. Over a matter of hours, the calcium and phosphorous ions may recrystallize on the surface of the larger particles in the form of hydroxycarbonate apatite, the physical crystalline structure in bone. As the crystalline layer forms, the body's proteins, including collagen, are attracted to and bind to the crystalline layer. This is thought to be the mechanism that accelerates the growth of fibrovascular tissue or bone within the bioglass macroporous structure.

Bioglass has been combined with solid implant materials such as the implant disclosed in the patent to Bonfield et al, U.S. Pat. No. 5,728,753 which teaches a combination of a polyolefin binder with bioactive glass that results in an implant structure that is strong and maintains flexibility. The bioactive glass is reported to promote interfacial bonding of the implant and surrounding tissues. The patent to Marotta, et al. U.S. Pat. No. 6,299,930 and the patent to Boyan, U.S. Pat. No. 5,977,204 teach the use of bioglass as a coating for implants.

Titanium, silicone, PMMA, ePTFE, and porous polyethylene can be made in rigid or semi-rigid form in a variety of shapes and sizes suited to a variety of reconstructive or aesthetic needs. Examples of such implants include augmentation shapes for recessive chins or cheekbones, stiff sheets to replace missing bone in the orbit or cranium, or even complex customized shapes to replace missing bone in the cranium, orbit maxilla, or other areas. The structural integrity of these materials is an important feature for many implant applications.

Titanium, silicone, PMMA and ePTFE are either solid or in the case of ePTFE, microporous. Microporous in this sense means having pores with an approximate average size under 60 microns in diameter. When these microporous materials are implanted in the body, the body forms a fibrovascular capsule around the implant, effectively walling it off from the body. If the material is soft or pliable, the capsule can contract, changing the shape of the implant. If the space inside the fibrovascular capsule becomes infected, the body's defense system cannot reach the infection, and the implant must be removed. Solid implants are also subject to long term migration, which may alter the desired effect of the implant. Some solid implants have been shown to cause resorption of the underlying bone, again changing the desired effect of the implant. Although solid implants are frequently coated with bioglass to improve interfacial bonding between surrounding tissues and the implant, solid implants do not allow tissues ingrowth and they are not fully integrated with the tissue of the body.

Hydroxyapatite is a natural material used as an implant and is resistant to infection. Hydroxyapatite has a porous structure and allows for tissue ingrowth. However, under some experimental conditions it has been established that hydroxyapitiate interfered with a normal host tissue response and led to chronic mild inflammation that did not completely resolve. Some additional drawbacks to the hydroxyapatite material are that it is abrasive, relatively heavy and must be carved from its natural state to conform to the shape and size of the void or desired shape. Furthermore, hydroxyapatite is relatively brittle and fragile and, due to these inherent mechanical properties, it is difficult to mechanically attach the implant material to the patient's surrounding tissue. Hydroxyapatite may be brittle and can crack at the interface between a screw and the implant material.

Porous polyethylene is a synthetic implant material that can be made with an interconnecting macroporous pore structure. Macroporous in this sense means pores above 100 microns in diameter. A macroporous interconnecting pore structure of porous polyethylene will allow the body to grow new vascularized tissue into the pore structure of the implant, thereby integrating it with the body rather than the body walling it off with a fibrous capsule. Such fibrovascular ingrowth allows the body's immune defenses to operate throughout the implant, to the extent that the implant becomes vascularized. Clinical observations and animal studies suggest that porous polyethylene is less likely to migrate within the body, and is less likely to cause resorption of the underlying bone. These advantages are generally thought to be due to the vascularization of the implant within the open porous structure.

Porous plastic or synthetic resin implants of a surgical grade polyethylene were developed which had a number of advantages over hydroxyapatite. These implants have superior strength, are light weight, and have proven to be effective in many of the applications which had been previously performed by hydroxyapatite materials. Porex Surgical of Newnan, Ga. manufactures such implant materials under the trademark MEDPOR® and markets products designed for implantation in a variety of shapes for a number of applications.

Porous polyethylene is an inert material which has the same advantages afforded by the porous surfaces provided by naturally occurring hydroxyapatite. The plastic is inert, stable and easily can be sterilized. Because the implant is synthetic, an uninterrupted supply of the material is readily available. Further, the material can be easily molded and shaped to appropriately fit a void or be altered to the desired shape. Lastly, because the porous material is flexible and pliable and may be compressed, it allows surgeons to employ coupling methods between the implant and the surrounding tissue. In view of these characteristics polyethylene has been successfully used for a number of years for surgical implant applications. MEDPOR Biomaterial allows for tissue ingrowth because of its interconnecting open pore structure. While the porous nature of the implant allows or permits such ingrowth, the nature of the material does not promote such growth. The firm nature of the material allows carving with a sharp instrument without collapsing the pore structure.

The porosity of MEDPOR Biomaterial is maintained large, with average pore sizes greater than 100 micro-meters and pore volume or the open space within said matrix is approximately in 40% to 60%. The MEDPOR biomaterial is intended for augmentation and restoration procedures in craniofacial applications and is provided in a anatomical shapes, sheets, blocks and spheres including preformed shapes for chin, nasal, malar and mandible augmentation. Blocks for cranial implants may be used for temporal and frontal contouring, as well as for reconstruction of surgical and traumatic defects. The material is also provided in sheets, wedges, and rims for orbital floor, enophthalmos and rim repair. MEDPOR is also made in spherical and conical shapes for enucleation and eviseration procedures.

While porous resin synthetic implants have many of the advantages described above, there are many patients and situations for which the use of synthetic implants may be problematic and can lead to early or late complications. These include: 1) replacement of the eye, where the implant is covered with relatively thin tissues and may be subject to early (within a few weeks) or late (a few weeks to a few years) tissue breakdown over the implant; 2) In diseased or irradiated tissues where healing is less than optimal; 3) where very large implants ace needed; and 4) where there is minimal or inadequate tissue to cover the implant. Particularly in these situations, there is an remains a need to have an implant material with good structural properties, the ability to be manufactured or modified to obtain a variety of shapes, and that has improved fibrovascular or bony integration properties in the body.

Vascularization of the porous implants minimizes the problems of migration and extrusion. Because non-porous implants have a higher incidence of failure due to infection and complications, porous implants are favored. Porous polyethylene implants have the advantage of allowing such tissue ingrowth. While such implants permit such vascularization and ingrowth, it is generally desirable to enhance or improve the vascularization and tissue ingrowth of such implants. While histologic analyses of biopsies from human implants have also demonstrated tissue ingrowth in MEDPOR implants, the clinical significance of tissue ingrowth may vary with the application and implant size. In this regard, magnetic resonance imaging of relatively large implants made of MEPPOR with relatively small surface areas indicates that these implants may not become completely vascularized throughout the implant even one full year after implantation. A method for accelerating fibrovascular ingrowth into such implants would be considered an improvement over the current art.

Accordingly, it is an object of the present invention to provide an improved implant material for cranio-maxillofacial reconstruction and augmentation.

In general, a macroporous implant material with good structural properties and improved fibrovascular integration properties would be considered an improvement over existing implant materials. More specifically, it is an object of the present invention to provide an implant material that has improved bone or fibrovascular ingrowth properties over those of presently available macroporous polyethylene.

It is yet a further object of the present invention to provide an implant material that has improved fibrovascular ingrowth properties and improved structural integrity over that of presently available bioglass implant materials.

It is a further object of the invention to provide an implant material that has improved fibrovascular ingrowth properties and the ability to be molded into a variety of shapes appropriate for cranio-maxillofacial reconstruction and augmentation.

It is a further object of the invention to provide an implant material that has improved fibrovascular ingrowth properties and can be easily modified with a blade or burr to adapt the shape to a particular defect site or to provide an appropriate amount of tissue augmentation.

It is a further object of the invention to provide an implant material that has improved fibrovascular ingrowth properties and that can be fixated to bone or other tissue using presently available fixation techniques.

It is a further object of the invention to provide an implant material that has improved fibrovascular ingrowth properties and that can be molded into customized shapes designed to fit individual patients.

These and other objects and advantages of the present invention will be more readily apparent with reference to the following detailed description and the accompanying drawings.

SUMMARY OF THE INVENTION

The present invention is directed to a composite implant made of a macroporous polyethylene having bioglass particles dispersed throughout the matrix. The implant material that has structural integrity, can be molded into a variety of shapes appropriate for cranio-maxillofacial augmentation or reconstruction, can be modified preoperatively or interoperatively with a blade or burr to adapt its shape to a particular defect site, and has improved fibrovascular ingrowth properties over presently available materials that have structural integrity. In accordance with the method of the present invention, an improved means of obtaining fibrovascular ingrowth into a macroporous polyethylene implant material is provided, by incorporating bioglass particles within the structure of the porous polyethylene implant material. The implant material is made by adding bioglass to a batch of polyethylene fines having a predetermined particle size range to a result in a mixture having approximately 10%–20% volume bioglass and the remainder polyethylene fines. The mixture is introduced to a mold and then subjected to heat and pressure to sinter the resin fines of the mixture together. The bioglass particles are retained within the resulting structure by both adhesion to the polyethylene particles and because they are mechanically trapped within the resulting matrix.

BRIEF DESCRIPTION OF THE DRAWINGS

FIG. 4a is a perspective front view of another embodiment of an implant according to the invention provided in a preformed in a shape that is useful for orbital reconstruction.

FIG. 4b. is a perspective rear view of the embodiment depicted in FIG. 4a.

DETAILED DESCRIPTION

In a preferred embodiment of the invention, synthetic resin fines are combined with approximately 12% bioglass and then sintered together to result in an porous implant having a matrix with bioglass distributed throughout the matrix. The structure can take the form of a wide variety of shapes, such as those described above and that are currently available from Porex Surgical, Inc. While porous polyethylene is a preferred synthetic polymer, it contemplated that other porous polymer materials can be advantageously used. The implant material is made by adding bioglass to a batch of polyethylene fines having a predetermined particle size that results in a mixture having approximately 10%–20% volume bioglass and the remainder polyethylene fines. Although increased volumes of bioglass may be used, the structural strength of the resulting implant diminishes as the ratio of bioglass is increased. In the preferred embodiment the size of the resin fines that are selected are roughly the same size as the silica particles in the bioglass. The size of the fines are also selected to result in an implant structure that allows for tissue ingrowth which has been found to be a median pore size of greater than approximately 100 microns.

Figure 1:
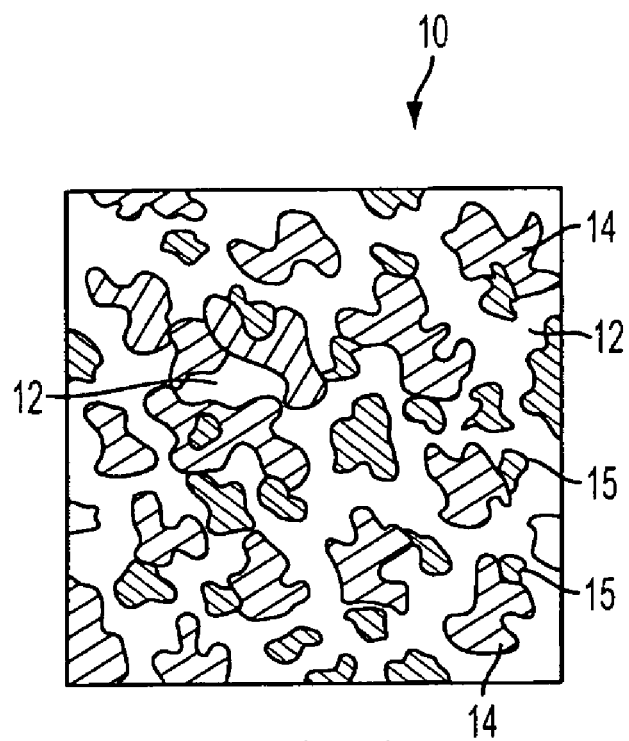
FIG. 1 is a schematic sectional view of the present invention, as it would appear under 50× to 100× magnification.

Referring now to FIG. 1, an schematic sectional view of the implant 10 is made of polyethylene 12 and as depicted shows a completely interconnected pore structure that exists throughout the implant. In this sectional view while it may appear that there are disconnected particles of polyethylene, they are part of an entirely connected structure, being connected at different levels within the material. Open space 14 within the polyethylene structure of the invention is an entirely interconnected open or intersticial spaces that permeate throughout implant 10. The channels distributed throughout the matrix are interconnected and extend in tortuous paths in numerous directions, or are omni-directional. For example, although some areas may appear to be closed off from the other open space in this view such as open space 14, the area is open to the remainder of the open space in different levels within the material. Dispersed throughout the implant are particles of bioglass 15, which are connected to the interconnected polyethylene structure 10 and mechanically entrapped within the implant matrix.

Figure 2:
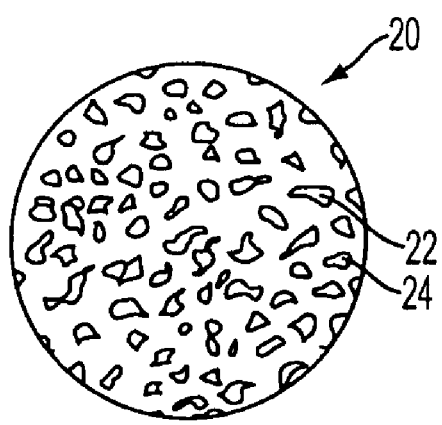
FIG. 2 is a perspective view of an implant having a spherical shape molded from the material of the present invention.

Referring to FIG. 2, the polyethylene implant structure 20 is seen on the surface of a molded spherical orbital implant shape that is intended to be used for volume augmentation after a surgical procedure to enucleate or eviscerate the eye. The interconnected open spaces within the polyethylene structure is seen as a series of holes 22 visible on the surface of the implant material. Also depicted in the surface are particles of bioglass 24 on the surface of the material.

Figure 3:
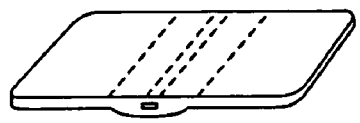
FIG. 3 is a perspective view of an implant according to the invention that has been provided in a thin sheet.
Figures 4A, 4B:
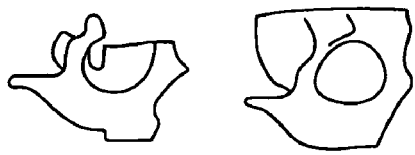
Figures 5A, 5B:
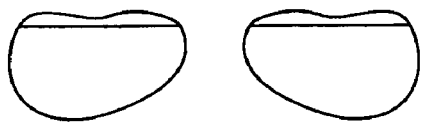
FIG. 5a is a perspective view of another embodiment of according to the invention provided in a preformed in a shape useful for reconstruction of the eyelid.
FIG. 5b is a perspective view of a complementary shaped to FIG. 5a of an implant shape useful for reconstruction of the eyelid.

FIG. 3 depicts an embodiment of the invention made in the shape of a thin sheet suitable for repair of the bones of the orbit or cranium. These sheets may be cut by the surgeon to fit the area of the defect. Referring now to FIGS. 4a and 4b, The present invention may be made in the shape of the human bony orbit or a portion of the human bony orbit suitable for repair of missing bone in the orbit as shown in FIGS. 4a and 4b. Referring now to FIGS. 5a and 5b depict a top view of a thin sheet of the implant materials that is suitable for support of a drooping eyelid.

Figure 6:
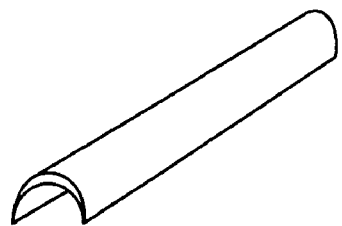
FIG. 6 is a perspective view of another embodiment of according to the invention provided in a preformed in a shape that is useful for reconstruction of the bridge of the nose.
Figure 7:
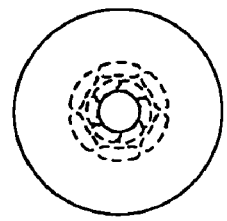
FIG. 7 is a perspective view of another embodiment of a according to the invention provided in a preformed in a shape that is useful for reconstruction of the cranium.

FIG. 6 depicts another embodiment of the invention wherein the implant material is preformed in the shape of a long arch, suitable for repair of a damaged or crooked nose. In implant suitable illustrated in FIG. 6 is according used to replace or augment cartilage. Another application is used to augment of replace portion of the dense bones of the cranium. FIG. 7 depicts an implant in the shape of a thin sheet with multiple projections extending perpendicular from the sheet. In application where a surgeon is repairing a hole in the cranium, the projections extend toward the cranial cavity and the thin sheet is attached to the skull at the periphery of the sheet with surgical screws or equivalent means.

Figure 8:
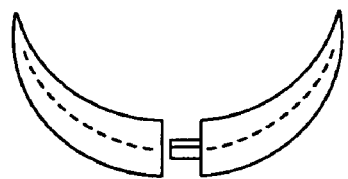
FIG. 8. is a perspective view of another embodiment of a according to the invention provide in a preformed shape that is useful for reconstruction or augmentation of the chin.

Referring now to FIG. 8, the present invention may also be made in the shape of a curved arch, in two connecting pieces, suitable for augmentation of the chin.

The various contemplated embodiments described above are not intended to be inclusive, but are intended to illustrate a small portion of the variety of shapes that may be fabricated using the present invention.

In use, to replace missing, resected or diseased tissue with an implant manufactured from the present invention, a surgical procedure is performed wherein the skin and overlying tissues of the defective area are incised and dissected away from the defect. The implant material, either preformed into the appropriate shape, or may be modified interoperatively in the sterile field of the operating theater to fit the defective area, is placed within the dissected area to replace missing or inadequate tissue. If appropriate, the implant may be fixed in the area by the use of surgical screws, wires, sutures or other appropriate means. The overlying tissues are repositioned over the implant, and closed according to standard surgical techniques. The particular shapes of the current invention and the structural integrity of the current invention support the overlying tissue to achieve the desired functional or aesthetic result for the patient. The accelerated fibrovascular ingrowth into the present invention provides for faster and more complete integration within the body, providing the advantages previously discussed.

While the preferred embodiment is comprised of a porous polyethylene implant material for cranio-maxillofacial implantation in non-load bearing areas, comprising a macroporous (greater than 100 microns in diameter) interconnecting porous structure, with bioglass particles dispersed throughout the porous polyethylene structure, other synthetic resins that other pore sizes that allow tissue ingrowth may also be employed. Further, while the percentage of bioglass is preferred to be between 10% and 20%, it is also contemplated that the relative proportion of bioglass may vary from approximately 1% to approximately 50% by weight. However, as the percentage of bioglass increases with respect to the percentage of polyethylene fines, the structural integrity of the resulting implant is correspondingly diminished. While the preferred application is for cranofacial reconstuction and augmentation, the implants may have applications to other areas of the body, such as use as a custom implant to augment underdeveloped areas of the chest cavity, or in connection with non-load bearing areas of the areas of the hip. It is further contemplated that the implant material may have applications in connection with the reconstruction of the ear and in connection with penile implants.

The invention provides desirable characteristics of both the macroporous polyethylene and bioglass materials into a single material. The porous polyethylene imparts the properties of biocompatibility, structural strength, light weight, an interconnecting macroporous structure, ease of handling, ease of shaping with a blade, burr or other cutting instrument, ease of manufacture in a variety of shapes, and low cost. The bioglass material provides the properties described above, including biocompatibility, compressive strength, hydrophilic properties, binding to healing tissue, and improved fibrovascular ingrowth.

The composite material retains the macroporous pore structure of macroporous polyethylene, some or most of the structural strength of porous polyethylene alone, and gains advantages including increased hydrophilic properties, binding to healing tissue, and improved fibrovascular ingrowth.

The invention involves combining the two materials in the above-mentioned proportions, and then manufacturing the materials in a similar fashion as one would manufacture porous polyethylene using polyethylene alone. (Greg—specifically . . . }

In a preferred contemplated embodiment of the invention Bioglass is added to the polyethylene base material in the form of granules ranging in particle diameter of approximately 100 to 900 microns. In another embodiment of the invention, the particle size range of the bioglass particles is selected to facilitate the optimum host response for the site of implantation and the type of tissue encountered in the site. The relative proportion of bioglass to porous polyethylene is may be selected to provide the optimum structural strength for the implantation application or the proportion can be selected to provide the optimum host tissue response for the site of implantation and the type of tissue encountered in the site.

While the preferred embodiments have been described herein, those skilled in the art will recognize that certain details may be changed without departing from the spirit and scope of the invention. Thus, the foregoing specific embodiments and applications are illustrative only and are not intended to limit the scope of the invention. It is contemplated that the invention will be functional and effective in applications where it is desirable to provide an implant material that is not required to bear significant load bearing properties. Likewise, although certain bioglass formulations, synthetic resins and pore sizes have been disclosed, and combinations thereof, it is contemplated that other formulations and resins may be selected to achieve the same or similar objectives.

I claim:

1. A porous surgical implant material for replacing or augmenting tissue in the body comprising a composite material made of an interconnected omni-directional porous matrix structure comprised of synthetic resin and bioactive glass particles distributed throughout said matrix
   wherein said porous matrix structure is formed by sintering together a plurality of synthetic resin fines and wherein said bioactive glass particles remain separate and distinct and are not sintered together during said sintering process.

2. The porous surgical implant material as recited in claim 1 further wherein said porous matrix has a porosity that permits vascularization and tissue ingrowth.

3. The porous surgical implant material as recited in claim 1 wherein said porous matrix has a porosity of approximately 100 to 500 microns.

4. The porous surgical implant material as recited in claim 1 wherein the pore volume is approximately 40 to 60 percent.

5. The porous surgical implant material as recited in claim 1 wherein said bioactive glass particles comprise silicon dioxide, sodium oxide, calcium and phosphorus oxide.

6. The porous surgical implant material as recited in claim 5 wherein said bioactive glass particles comprise approximately 45% silicon dioxide, 45% sodium oxide, and the remaining 10% calcium and phosphorus oxide.

7. The porous surgical implant material as recited in claim 1 wherein said synthetic resin comprises polyethylene.

8. The porous surgical implant material as recited in claim 7, wherein the matrix is characterized by a pore volume of 40% to 60%.

9. The porous surgical implant material as recited in claim 1, wherein the matrix comprises 1–50% bioglass.

10. The porous surgical implant material as recited in claim 1, wherein the matrix comprises 10–20% bioglass.

11. The porous surgical implant material as recited in claim 7, wherein the matrix comprises 1–50% bioglass.

12. The porous surgical implant material as recited in claim 7, wherein the matrix comprises 10–20% bioglass.

13. The porous surgical implant material as recited in claim 9 wherein said bioactive glass particles comprise silicon dioxide, sodium oxide, calcium and phosphorus oxide.

14. The porous surgical implant material as recited in claim 13, which is characterized by a pore volume of 40–60%.

15. The porous surgical implant material as recited in claim 1 wherein said matrix structure is flexible.

16. A porous surgical implant material for replacing or augmenting tissue in the body comprising a composite material made of an interconnected omni-directional porous matrix structure comprised of synthetic resin and bioactive glass particles distributed throughout said matrix and said matrix structure of said implant is formed in the absence of a poragenic material and wherein said porous matix is formed by the sintering of synthetic resin fines together.

17. The porous surgical implant material as recited in claim 16 where said synthetic resin fines comprise polyethylene.

18. The porous surgical implant material as recited in claim 16 further wherein said porous matrix has a porosity that permits vascularization and tissue ingrowth.

19. The porous surgical implant material as recited in claim 16 further wherein said porous matrix is macroporous.

* * * * *